United States Patent [19]

Rogić et al.

[11] 4,206,112

[45] Jun. 3, 1980

[54] α-NITROSOKETAL DIMERS AND PRODUCTION OF α-OXIMINOKETALS THEREFROM

[75] Inventors: Milorad M. Rogić, Whippany; Michael D. Swerdloff, Parsippany; Timothy R. Demmin, Morris Plains, all of N.J.

[73] Assignee: Allied Chemical Corporation, Morris Township, Morris County, N.J.

[21] Appl. No.: 968,935

[22] Filed: Dec. 13, 1978

Related U.S. Application Data

[60] Division of Ser. No. 807,692, Jun. 17, 1977, abandoned, which is a division of Ser. No. 600,666, Jul. 31, 1975, Pat. No. 4,045,422, which is a continuation-in-part of Ser. No. 460,836, Apr. 15, 1974, abandoned.

[51] Int. Cl.$^2$ .................. C07C 105/00; C07C 131/00
[52] U.S. Cl. ................................ 260/143; 260/566 A
[58] Field of Search ........................... 260/566 A, 143

[56] References Cited

PUBLICATIONS

Klein et al., J. Organic Chem., vol. 44, pp. 275–285 (1979).
Rogic et al., J. Am. Chem. Soc., vol. 99, pp. 1156–1171 (2/16/77).
Smith, "The Chemistry of Open-Chain Organic Nitrogen Compounds", vol. II, pp. 355–362 (1966).
Rogic et al., J. Am. Chem. Soc., vol. 97, p. 3241 (1975).

*Primary Examiner*—Norman P. Morgenstern
*Assistant Examiner*—L. Hendriksen
*Attorney, Agent, or Firm*—Robert A. Harman

[57] ABSTRACT

This invention describes novel ketals of α-oximinoketones, methods for the preparation of these compounds and includes novel intermediates formed during the production thereof. The novel class of compounds disclosed herein includes both α-oximinoketals, as well as the cyclic ketals of α-oximinoketones. This invention also discloses a novel class of α-nitrosoketal dimers produced during the synthesis of the corresponding α-oximinoketals, and it also discloses novel methods in the production thereof.

8 Claims, No Drawings

α-NITROSOKETAL DIMERS AND PRODUCTION OF α-OXIMINOKETALS THEREFROM

CROSS REFERENCE TO RELATED APPLICATIONS

This application is a division of our copending application Ser. No. 807,692 filed June 17, 1977 now abandoned; which in turn was a division of our application Ser. No. 600,666 issued Aug. 30, 1977 as U.S. Pat. No. 4,045,422 filed July 31, 1975 as a continuation-in-part of our application Ser. No. 460,836 filed Apr. 15, 1974 now abandoned.

FIELD OF THE INVENTION

This invention describes novel ketals of various α-oximinoketones, methods for the preparation of these compounds and includes novel intermediates formed during the production thereof. This invention also discloses a novel class of α-nitrosoketal dimers, which can be regarded as the intermediates in the production of the corresponding α-oximinoketals, and particularly it discloses novel methods for the production of the said α-nitrosoketal dimers.

Beckman fragmentation of these novel ketals of α-oximino ketones, particularly those of α-oximinocyclohexanone, α-oximinocyclopentenone, α-oximinocyclooctanone, α-oximinocyclodecanone, etc. provides the corresponding alkyl ω-cyanoalkanoates which are convenient intermediates for the production of either cyclic lactams or polyamides and amino acids. Similarly, direct nitrosolysis of the corresponding α-nitrosoketal dimers provides the same alkyl ω-cyanoalkanoates as above.

SUMMARY OF THE INVENTION

The novel α-nitrosoketal dimers, which can be used as intermediates for the synthesis of the α-oximinoketals, may be characterized by the formula:

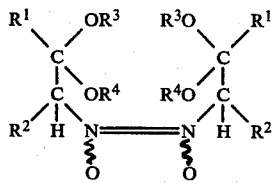

which for convenience of notation will henceforth be written as:

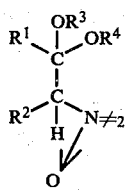

with an implicit understanding that the corresponding dimer may be either a dl-pair, or meso compound of either Z- or E-dimers where Z- and E- refer to the cis- or trans- configuration of the two oxygen atoms attached to the N=N grouping, wherein: $R^1$ and $R^2$ are selected from the group consisting of $C_1$-$C_{10}$ alkyl or phenyl and/or combinations thereof, and $R^3$ and $R^4$ are independently selected from the group consisting of $C_1$-$C_{10}$ alkyl, cyclohexyl and $C_1$-$C_4$ alkyl substituted cyclohexyl radicals.

The novel ketals of α-oximinoketones described in the present invention may be characterized by the following formula:

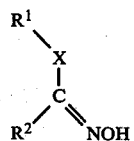

wherein: $R^1$ and $R^2$ are selected from the group consisting of $C_1$-$C_{10}$ alkyl or phenyl and/or combinations thereof, or in combination together represent a part of the $C_5$-$C_{12}$ cyclic ring structure; and X is a member of the group consisting of:

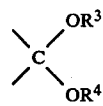

wherein $R^3$ and $R^4$ are independently selected from the group consisting of $C_1$-$C_{10}$ alkyl, cyclohexyl and $C_1$-$C_4$ alkyl substituted cyclohexyl radicals.

Illustrative nitrosoketal dimers include:

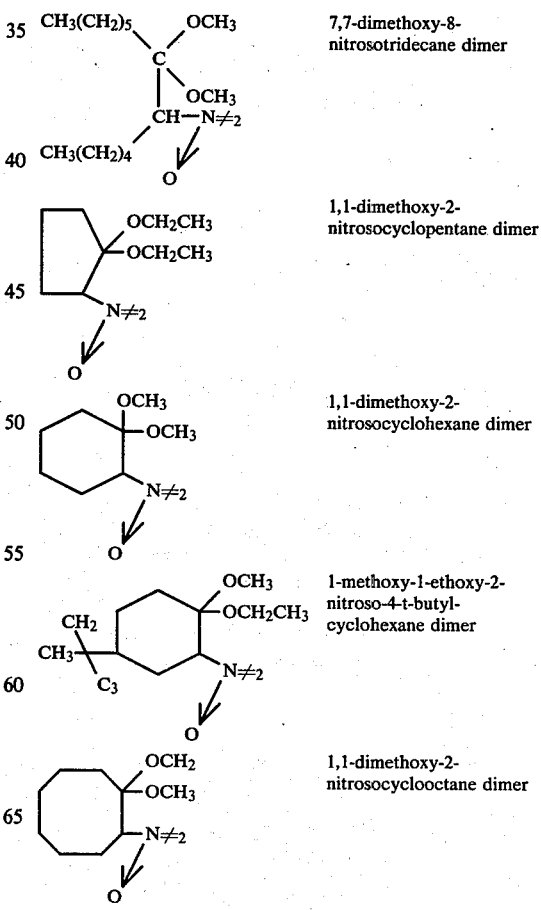

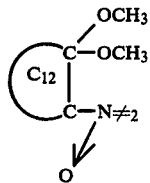 1,1-dimethoxy-2-nitrosocyclododecane dimer

Illustrative α-oximinoketal compositions include:

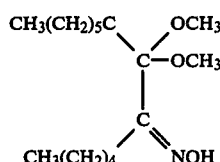 7,7-dimethoxy-8-oximinotridecane

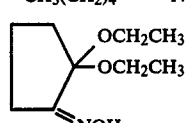 1,1-dimethoxy-2-oximinocyclopentane

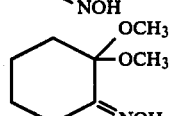 1,1-dimethoxy-2-oximinocyclohexane

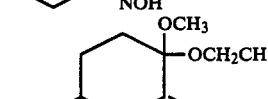 1-methoxy-1-ethoxy-2-oximino-4-t-butyl-cyclohexane

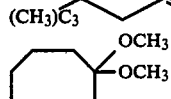 1,1-dimethoxy-2-oximinocyclooctane

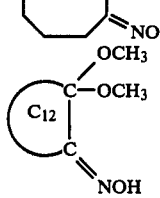 1,1-dimethoxy-2-oximinocyclododecane

The novel dimer compositions of the present invention may be prepared by nitrosating alkoxyalkenes of the formula:

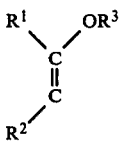

wherein: $R^1$ and $R^2$ are selected from the group consisting of $C_1$–$C_{10}$ alkyl or phenyl and/or combinations thereof, or in combination together represent a part of the $C_5$–$C_{12}$ cyclic ring structure, and $R^3$ is selected from the group consisting of $C_1$–$C_{10}$ alkyl, cyclohexyl, and $C_1$–$C_4$ substituted cyclohexyl radicals; with at least one molar equivalent of an alkyl nitrite of the formula $$R^4ONO$$

either in the absence of other solvents, or in an inert solvent in either case in the presence of catalytic amounts of a suitable acid catalyst, wherein $R^4$ is selected from the group consisting of $C_1$–$C_{10}$ alkyl, cyclohexyl and $C_1$–$C_4$ alkyl substituted cyclohexyl radicals, and isolating the dimer product(s) thus formed.

These dimers may be readily converted to the corresponding α-oximinoketals by isomerizing the dimers and isolating desired products.

However, in accordance with the method of the present invention, it is not necessary to isolate and purify the dimer product in order to produce the desired oximino ketal product. Thus, satisfactory yields of the α-oximinoketals may be obtained by nitrosating the previously described alkoxyalkenes either with an excess of an alkyl nitrite in the absence of other solvent, or in an inert solvent, removing the excess of alkyl nitrite, adding an inert solvent, isomerizing the remaining residue, and isolating the desired product.

In addition to producing these novel α-oximinoketals by nitrosating with alkyl nitrites and isomerizing, it is possible to perform the desired nitrosation using at least one molar equivalent each of a nitrosyl halide, a base and an alcohol of the formula $R^4OH$ where $R^4$ is as previously defined; and isolating the desired product.

DESCRIPTION OF THE PREFERRED EMBODIMENTS

In accordance with the method of the present invention, the novel α-nitrosoketal dimers are produced by the nitrosation of the corresponding alkoxyalkenes. The novel α-oximinoketals are produced either by isomerization of the corresponding nitroso dimers, or directly from the alkoxyalkenes by nitrosation and isomerization without isolation of the intermediates involved. Additionally, the novel cyclic ketals of α-oximinocyclohexanone can be produced directly from cyclohexanone by nitrosation in the presence of a suitable vicinal diol.

The alkoxyalkenes used as starting materials in this invention may be prepared using a variety of methods such as by the acid catalyzed elimination of the alcohol from the corresponding ketals, as represented by the equation:

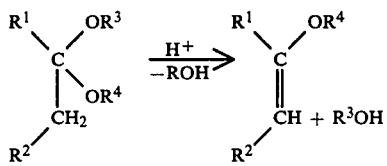

wherein $R^1$, $R^2$, $R^3$ and $R^4$ are as previously defined. Thus $R^1$ and $R^2$ may be any $C_1$–$C_{10}$ alkyl radical, phenyl group, or in combination together may be a part of $C_5$–$C_{12}$ cyclic structure.

The nitrosation of alkoxyalkenes may be carried out using at least one molar equivalent, preferably 3–10 molar equivalent of a suitable nitrosating reagent in the absence of other solvent and in the presence of a catalytic amount, preferably between 0.01–0.1 molar equivalent, of a suitable acid. Suitable nitrosating agents include alkyl nitrites of the formula $R^4OHO$, where $R^4$ is as previously defined. The suitable acid catalysts are sulfur trioxide, sulfuric acid, oleum, boron trifluoride etherate, alkyldialkoxycarbonium fluoroborates, preferably boron trifluoride etherate or alkyldimethoxycarbonium fluoroborates.

Thus, preparation of the corresponding α-nitrosoketal dimers may be represented with the equation:

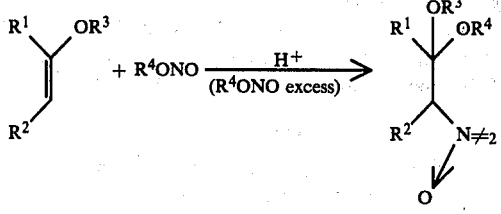

wherein $R^1$, $R^2$, $R^3$ and $R^4$ are as previously defined. The nitrosation reaction may be carried out between $-70°$ to $+25°$, preferably at $-30°$ to $0°$, and would depend on particular system employed. The isolation of the nitroso dimer may be accomplished either by filtration or by evaporation of the excess of the alkyl nitrite used.

Alternatively, the nitrosation reaction with alkyl nitrites may be carried out in any suitable inert solvent using only one, preferably 1.10–1.20 molar equivalents of an alkyl nitrite and the suitable acid catalyst. Suitable solvents include ether, chloroform, organic sulfones, organic nitro compounds, etc., however, liquid sulfur dioxide is preferred. The amount of solvent employed should be sufficient to bring the desired course of the reaction. When solvents other than sulfur dioxide are employed, the presence of acid catalyst, e.g. sulfur trioxide, sulfuric acid, boron trifluoride etherate, is required; when sulfur dioxide is employed, such a catalyst is preferred but not essential to the course of the reaction.

The nitrosation with alkyl nitrites in the presence of a solvent may be carried out using a wide range of temperatures, depending on the solvent used and the nature of the alkyl nitrite. Using $SO_2$ as solvent, the preferred temperature range is between $-30°$ and $+25°$ C., although the temperature between the freezing and boiling points of the solvent could be used. Similarly, nitrosation with alkyl nitrites in the absence or in the presence of other solvent, may be carried out either at atmospheric pressure or higher, preferably between atmospheric pressure and 200 psi.

If recovery of the thus formed nitroso dimer is desired, it may be readily isolated by evaporation of the solvent (including the excess alkyl nitrite), in the presence of small amount of sodium bicarbonate or other base which is added to assure the neutralization of any acid catalyst used. The desired material is then recovered by filtering from a solvent in which the particular nitroso dimer has little or no solubility.

The isomerization of thus produced nitroso dimers to the corresponding α-oximinoketals may be carried out with or without the previously described isolation of the dimer. This isomerization may be accomplished using a variety of methods, and can be schematically represented by the following equations:

In accordance with the present invention, the dimer may be heated above its melting point until such time as the color of the melt changes from blue, indicative of the presence of the corresponding monomeric nitroso compound, to either colorless or slightly yellow. Subsequent cooling provides the desired α-oximinoketals which can be further purified by conventional technique.

Alternatively, the nitroso dimers may be isomerized by heating in solvents, such as pentane, benzene, heptane, toluene, methanol, ethanol, chloroform, etc., at a temperature below the melting point of the compound. A further isomerization procedure comprises a catalytic reaction using either inert or hydroxylic solvents as above in the presence of a catalytic amount of base. In this case the isomerization can be accomplished either at room temperature or by heating.

If the preparation of the nitroso dimer is carried out in a solvent and the dimer is not isolated, the isomerization can be achieved by heating the reaction mixture after completion of the nitrosation reaction, either in the presence of the acid catalyst used in the nitrosation reaction, or under slightly basic conditions after neutralization of the acid catalyst with various bases, such as metal alkoxides. Alternatively, in accordance with the preferred method, the sulfur dioxide or excess alkyl nitrite, is displaced by a solvent such as methanol, ethanol, pentane, benzene, heptane, toluene, or chloroform, and the isomerization is then achieved by heating, or as described above, in the presence of catalytic amount of base. In either case, the desired α-oximinoketal is isolated after removal of solvent, as for example, by crystallization.

In the case of nitrosation of alkoxyalkenes with a nitrosyl halide, preferably nitrosyl chloride, a corresponding halo substituted compound is formed as an intermediate which is then treated, without isolation, in the presence of at least one molar equivalent of each of base and an alcohol of the formula $R^4OH$ where $R^4$ is as previously defined. Preferably 2–3 molar equivalents of the alcohol are employed. Alternatively, the nitrosation reaction may be carried out in the presence of the alcohol, in which case the base is added after complete addition of the nitrosyl halide and worked-up as before.

Schematically, this reaction may be represented by the following equations using nitrosyl chloride as the nitrosating reagent.

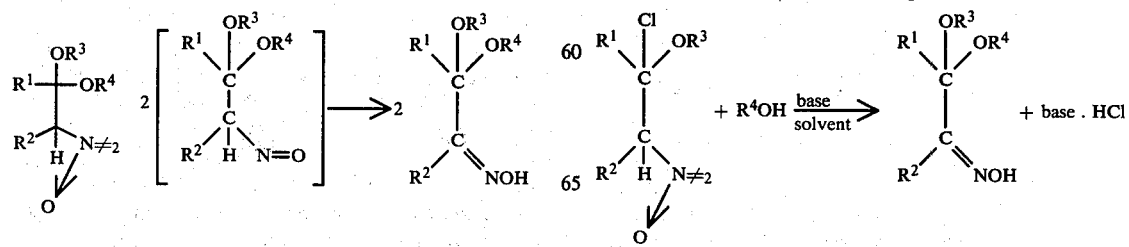

wherein $R^1$, $R^2$, $R^3$ and $R^4$ are as previously described.

wherein $R^1$, $R^2$, $R^3$ and $R^4$ are as previously defined. This reaction may be carried out in any of the previously disclosed inert solvents; however, the preferred solvent for this particular reaction is ether. Suitable bases include sodium methoxide, pyridine, triethylamine, and preferably a solution of sodium hydroxide in the $R^4OH$ alcohol. The reaction temperature is not critical and preferably, when ether is used as solvent, will be between −20° and 30° C. Pressures within the range of one atmosphere to 200 psi may be employed. The reaction time is not critical and is selected to ensure complete reaction. After separation of the halide salt the reaction product, the corresponding α-oximinoketal, may be isolated by evaporation of the solvent and crystallization.

The invention will be further illustrated by the following Examples.

EXAMPLE 1

Production of 1,1-dimethoxy-2-nitrosocyclohexane dimer using excess of methyl nitrite as solvent Methyl nitrite (125 g, 2.05 mole) was distilled into a 500 ml flask equipped with a mechanical stirrer, addition funnel, dry ice condenser, $N_2$ atmosphere and a bath maintained at −20° C. 20% Oleum (0.325 ml, 1 mole % based on amount of 1-methoxycyclohexene used) was added. 1-Methoxycyclohexene (75.4 g, 0.674 mole) was added dropwise over 2.5 hours with stirring. The reaction mixture was a heavy suspension of a white solid in a blue-green liquid. The catalyst was neutralized by sodium bicarbonate (6.5 g) with the addition of petroleum ether (b.p. 30°–60° C.) to facilitate stirring. Excess methyl nitrite was allowed to distill off, and the reaction mixture filtered and the white solid washed with petroleum ether. Evaporation of the filtrate in vacuum is carried out to recover partially dissolved product. The combined crude solid dimer, 113.8 g, was according to nmr analysis essentially pure 1,1-dimethoxy-2-nitrosocyclohexane dimer. The inorganic materials can be removed by dissolving the crude dimer in freshly distilled methylene chloride, filtering and removing the solvent at 0° C. Such a dimer is white powder m.p. 108°–110°.

EXAMPLE 2

Production of 1,1-dimethoxy-2-nitrosocyclohexane dimer

Methyl nitrite (29.75 g., 0.487 mole) was distilled into 250 ml. of sulfur dioxide maintained at −78° C. in a 1000 ml. three-neck flask equipped with a mechanical stirrer, an addition funnel-dry nitrogen inlet and a dry-ice/acetone condenser. Freshly distilled boron trifluoride-etherate (0.25 ml., 0.28, g., $2.0 \times 10^{-3}$ mole) was quickly added via syringe and the light yellow solution was warmed to −15° C. with a bath of dry ice/carbon tetrachloride. The nitrogen inlet was then placed in the condenser and 1-methoxycyclohexane (45.8 g., 0.407 mole) was added dropwise over 20 minutes to the stirred reaction mixture. After the addition was complete, stirring was continued for an additional 20 minutes at −15° C. and the deep blue-green solution rapidly turned a light yellow-green. The cooled (−78° C.) reaction mixture was quickly poured into 200 ml. of cold pentane containing sodium bicarbonate (1-2 g.) and then thoroughly evaporated at 20° C. The yellow-green gummy residue was triturated with several portions of pentane (150 ml. each) at 0° C., re-evaporated each time, and finally allowed to warm to room temperature under 300 ml of pentane with occasional swirling over 45 minutes. The off-white solid was filtered, rinsed with cold pentane, stirred with 150 ml. of water at 0° C. and then filtered and dried in vacuo to give 35.4 g. (50.1%) of the nitroso dimer, m.p. 108°–110° C.

EXAMPLE 3

(a) Preparation of Ethyldimethoxycarbonium Fluoroborate Catalyst*

In a dry reactor with an argon atmosphere, trimethylorthopropionate (b.p. 122°–125° C., 11.3 g., 84.3 moles) is cooled to −30° C. A mixture of $BF_3.Et_2O$ (12.3 ml., 94.4 mmoles) and dry dichloromethane (10 ml.) is added over a 15 minute period with stirring. The reactor is warmed to ice-water bath temperature for 15 minutes. Dry ethyl ether (15 ml) is added and the reaction mixture is cooled to −70° C. The solvents are decanted from the solid, brown product which is then washed at −70° C. with a mixture of dichloromethane (10 ml.) and ethylether (10 ml.). After decantation, the product is dried at RT/<1 mm Hg to an off-white solid. It is dissolved in dichloromethane (30 ml) to a yellow-brown solution and stored at RT under a slight pressure of argon. Its concentration was determined to be two mmole/ml by the use of nmr and an internal standard (chloroform). When used as a catalyst an aliquot is removed by syringe. The structure

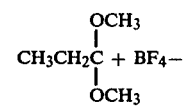

was confirmed by nmr.

*In preparing this catalyst the procedure disclosed in R.F. Borch JOC, Vol. 34, No. 3, p. 627, March (1969) R.F. Borch, JACS /90:19/Sept. 11 (1968), p. 5303 was utilized.

(b) 1,1-dimethoxy-2-nitrosocyclohexane dimer was prepared by the procedure described in Example 1 with the exception that one mole percent diethoxycarbonium fluoroborate was used as a catalyst. The essentially pure dimer was recovered as product and its structure was confirmed by IR and nmr.

EXAMPLE 4

1-Ethoxy-1-methoxy-2-nitrosocyclohexane dimer was prepared according to the procedure described in Example 1 from the reaction of 1-ethoxycyclohexene (20.4 g., 0.162 moles) and excess methylnitrite (2.5 g., 0.414 mole). In this instance, only about 25% of the dimer (5.9 g.) was recovered as precipitate with the major portion (18.9 g.) being recovered by flash evaporation of the wash liquors at 25° C. The recovered products were essentially the same and IR and nmr confirmed the structure as being essentially pure dimer.

EXAMPLE 5

1,1-Dimethoxy-2-nitrosocyclopentane dimer was prepared as in Example 1 by reacting 1-methoxycyclopentene (15.9 g., 0.162 mole) with an excess of methylnitrite (29.7 g., 0.48 mole) using 0.5 mole percent of 20% oleum as catalyst. The product (20.5 g.) was mostly the desired dimer with a small amount of 1,1-dimethoxy-2-oximinocyclopentane. An additional 5 grams of product were recovered by flash evaporation of the wash liquors. The structure was confirmed by IR and nmr.

When the product was allowed to stand for four days at room temperature in chloroform, it rearranged to 1,1-dimethoxy-2-oximinocyclopentane mp 79°–80° containing some methyl ester of 3-cyanobutyric acid.

EXAMPLE 6

Using the procedure described in Example 1, 1,1-dimethoxy-2-nitrosocyclooctane dimer was prepared by reacting 1-methoxycyclooctene (18.5 g., 0.132 mole) with an excess of methylnitrite (25 g., 0.406 mole) in the presence of one mole percent of 20% oleum (0.065 ml) as catalyst. The precipitated dimer (17.5 grams) was recovered in the usual manner and its structure was confirmed by IR and nmr. An additional amount (10.6 g.) of dimer was recovered by flash evaporation of the wash liquors at ice-water temperature.

EXAMPLE 7

Using the procedure described in Example 1, 1,1-dimethoxy-2-nitrosocyclododecane dimer was prepared by reacting 1-methoxycyclododecene (25.8 g., 0.132 mole) with an excess of methylnitrite (25 g., 0.406 mole) in the presence of one mole percent of 20% oleum (0.065 ml) as catalyst. The structure of the dimer recovered (27.4 g.) was confirmed by IR. This dimer was not soluble in chloroform, methanol, dichloromethane, 1,2-dichloroethane, isopropanol, DMSO, cyclohexane, nitromethane or benzene at room temperature. An additional 7 g. of product was recovered from the wash liquors.

EXAMPLE 8

Using the procedure described in Example 1, 2-methoxycamphene (18.9 g., 0.114 mole) was reacted with an excess of methylnitrite (25 g., 0.406 mole) in the presence of one mole percent of 20% oleum as catalyst. There was no indication of blue coloration (nitroso compounds) or a precipitate during the course of the reaction. After neutralization with sodium bicarbonate, the solvents were removed by flash evaporation yielding a pale yellow liquid (13.4 g). The yield is low due to analyses during the course of the run and also the possibility of volatilization during the evaporation of the solvents. IR and nmr indicate a mixture of products. The following components were identified by Finigan Mass Spec:

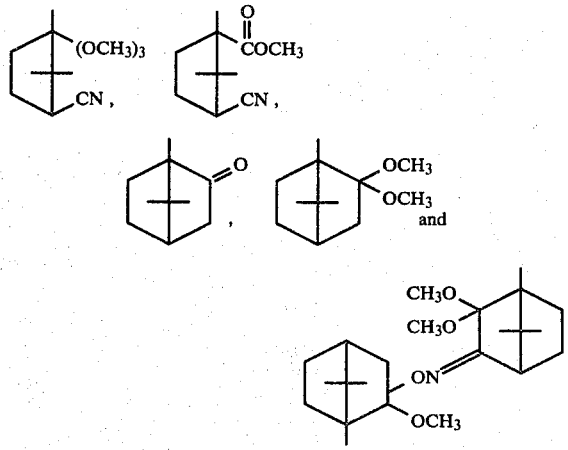

There was no evidence for 2,2-dimethoxy-3-oximinocamphor or 2,2-dimethoxy-3-nitrosocamphor or its dimer.

EXAMPLE 9

Using the procedure described in Example 1, 2,2-bis-(4-methoxycyclohex-2-enyl)propane (5 g., 0.0378 mole) was reacted with an excess of methylnitrite (25 g., 0.406 mole) in the presence of one mole percent of ethyldimethoxycarbonium fluoroborate as catalyst. While the reaction mixture was blue-green in color, there was no precipitate formed. The reaction mixture was neutralized with sodium bicarbonate and the excess methylnitrite was distilled from the reactor and stored for later reactions. The solid product was dissolved in 50 ml dichloromethane and filtered to remove inorganics. The product (7.1 g. pale green solid) was recovered by flash evaporation of the solvent. The nmr spectrum is compatible with the nitroso dimer structure but the IR also indicates the presence of nitroso groups. This is probably indicative of difficulties encountered in working with systems that can polymerize since possibly all of the nitroso groups cannot dimerize due to steric factors.

EXAMPLE 10

Using the procedure described in Example 1, attempted preparation of the 7,7-dimethoxy-6-nitrosotridecane dimer was carried out by reacting 7-methoxytridec-7-ene (28 g., 0.132 mole) with an excess of methylnitrite (25 g., 0.406 mole) in the presence of one mole percent of ethyldimethoxycarbonium fluoroborate as catalyst. After neutralization of the catalyst with sodium bicarbonate, the excess methylnitrite was recovered by distillation. The reaction residue was dissolved in pentane (25 ml) and filtered to remove the inorganic material. On flashing off the pentane, a product (24.2 g.) was recovered which was not the dimer but mostly 7,7-dimethoxy-6-oximinotridecane. This structure was confirmed by nmr and IR. IR also indicates the presence of some carbonyl containing product which could be the methylester of octanoic acid. The yield of product is lower due to the removal of reaction mixture for analysis during the course of the reaction.

EXAMPLE 11

Using the procedure described in Example 10, a mixture (18.75 g., 0.135 mole) of 2-methoxyoct-2-ene (80%) and 2-methoxyoctene (20%) was reacted with an excess of methylnitrite (25 g., 0.406 mole) in the presence of one mole percent of ethyldimethoxycarbonium fluoroborate as catalyst. The product (23.3 g.) was a yellow liquid which, by nmr analysis, did not contain any dimer but was mostly a mixture of 3,3-dimethoxy-2-oximinooctane and 2,2-dimethoxy-1-oximinooctane. IR indicates the presence of an ester function which could mean that further reaction of the oximes may have taken place.

EXAMPLE 12

1,1-Dimethoxy-2-nitrosocyclohexane dimer (59.3 g.) as prepared in Examples 1 or 2 was dissolved in dichloromethane (200 ml) and allowed to stand at room temperature for three days. The tan solution was treated with decolorizing charcoal and filtered through a celite cake in an attempt to remove colored impurities. This was not successful. After flashing off the dichloromethane, the tan product (49.1 g.), m.p. 115°–116°, was essentially pure 1,1-dimethoxy-2-oximinocyclohexane by nmr and IR analysis.

EXAMPLE 13

Production of 1,1-dimethoxy-2-oximinocyclochexane 1,1-Dimethoxy-2-nitrosocyclohexane dimer (25.0 g., 72.2 mmole) prepared in Example 1 was suspended in 175 ml. of methanol and then made basic to pH 8 with sodium methoxide. The reaction mixture was stirred at 50° C. under a dry nitrogen atmosphere for 1½ hours. After reducing the volume to 75–100 ml. on a rotary evaporator and slowly cooling to −20° C., the oxime was filtered off directly as clear colorless needles, 15.6 g., m.p. 116°117°. An additional crop of slightly impure crystals, 4.2 g., m.p. 108°115°, was collected by recrystallizing the residue from ether/pentane at −70° C. Total yield of oxime was 19.8 g. (79.2%).

EXAMPLE 14

1,1-Dimethoxy-2-nitrosocyclododecane dimer as prepared in Example 7, (31 g.) was heated (95° C.) in dry toluene (300 ml) for 1.5 hours with 150 mg. NaOCH$_3$ as catalyst. The suspended solid slowly dissolved in the blue-green reaction mixture which finally became yellow indicating that all of the nitroso groups had reacted. The cool reaction mixture was filtered through celite to remove inorganic material and the toluene was removed by flash evaporation. The cream colored solid (29.9 g.) was confirmed as 1,1-dimethoxy-2-oximinocyclododecane by nmr.

With more soluble nitroso dimers, such as 1,1-dimethoxy-2-nitrosocyclohexane, anhydrous methanol can be used as solvent in the above reaction. 1,1-Dimethoxy-2-nitrosocyclododecane was refluxed in methanol with catalytic quantities of sodium methoxide and was recovered unchanged. When n-butanol (b.p. 118° C.) was used as solvent, the conversion to the oxime took place within 0.5 hours. However, there was interchange of butoxy groups for methoxy groups in the oxime so the use of n-butanol as solvent was discontinued.

EXAMPLE 15

2,2-Bis(4-methoxy-3-nitrosocyclohexyl)propane dimer (1 g.) as prepared in Example 9, was heated in dry toluene (10 ml) in the presence of catalytic amount of sodium methoxide. The bluegreen solution turned yellow and a precipitate formed. The reaction mixture was refluxed for three hours. The light tan precipitate (0.57 g.) was reovered by filtration and IR indicates it is mainly 2,2-bis(4-methoxy-3-oximinocyclohexyl)propane. The filtrate was flash evaporated and the residue (0.2 g.) was similar to the starting nitroso dimer by nmr and IR analysis.

EXAMPLE 16

1,1-Dimethoxy-2-nitrosocyclooctane dimer (18.3 g.), prepared according to Example 6, was dissolved in dry toluene (150 ml.) at 45° C. and catalyzed with about 150 mg. of sodium methoxide. Within five minutes, the deep blue color changed to yellow and a reaction exotherm caused the temperature to rise to 56° C. The reaction mixture was stirred at ambient temperatures for 2.5 hours and the toluene flashed off after filtering off the inorganic materials using a celite cake. The pale yellow solid (15.3 g.) was identified as 1,1-dimethoxy-2-oximinocyclooctane by IR and nmr analysis. Some was lost during the filtration.

EXAMPLE 17

1,1-Dimethoxy-2-oximinocyclohexane was produced directly from 1-methoxycyclohexane and methyl nitrite using the following procedure:

1,1-Dimethoxy-2-nitrosocyclohexane dimer was prepared as described in Example 1 from 1-methoxycyclohexene (46.8 g., 0.417 mole), methyl nitrite (30.6 g., 0.501 mole) and boron trifluoride-etherate (0.25 ml., 0.28 g., 2.0×10$^{-3}$ mole) in 250 ml. of sulfur dioxide. The crude nitroso dimer, 76.0 g. of a gummy yellow-green solid still containing traces of sulfur dioxide, was obtained by the method described earlier. Without purification, the dimer was subjected to isomerizing conditions in methanol/sodium methoxide solution. Filtration through celite (to remove colloidal solids that had formed) and evaporation afforded 66.0 g. of an off-white slightly moist solid. Recrystallization from 180 ml. of ether at −70° C. gave 26.8 g. (37.2%) of 1,1-dimethoxy-2-oximinocyclohexane as colorless fine needles, m.p. 112°–116° C. An additional 2.9 g. (4.0%) of slightly impure oxime was obtained from the mother liquor as a white powder, m.p. 105°–112° C.

EXAMPLE 18

1,1-Diethoxy-2-oximinocyclohexane was produced directly from 1-ethoxycyclohexene and nitrosyl chloride using the following procedure.

1-Ethoxycyclohexene (6.3 g., 50 mmole) was added to 100 ml. SO$_2$ maintained at about −50° C. Then 4.4 ml. (75 mmole) ethanol were added after which 3.2 ml. (70 mmole) nitrosyl chloride was added as a gas. When addition of the nitrosyl chloride was completed, the reaction mixture was concentrated, chloroform was added and the solution neutralized, with sodium bicarbonate in the presence of a small amount of water. The product was filtered and the crystals analyzed by nmr to indicate the presence of a major proportion of the desired product.

EXAMPLE 19

The procedure of Example 18 was repeated using ethyl ether as a solvent in place of SO$_2$. When the reaction was complete, the mixture was treated with additional ether, solid sodium bicarbonate and a small amount of water. The crystals collected after filtration and evaporation were examined by nmr and found to consist essentially of 1,1-diethoxy-2-oximinocyclohexane.

EXAMPLE 20–22

Methods similar to those employed in Examples 2 and 17–19 can be used to produce the following novel compounds.

| Example | Ether | Nitrosating Agent | Product |
|---|---|---|---|
| 20 | 1-methoxy-4-t-butylcyclohexene | ethyl nitrite | 1-methoxy-1-ethoxy-2-oximino-4-t-butylcyclohexane |
| 21 | 1-methoxy-5-phenylcyclohexene | NOCl + 4-methylcyclohexanol | 1-methoxy-5-phenyl-1-(4'-methylcyclohexyloxy)2-oximinocyclohexane |

-continued

| Example | Ether | Nitrosating Agent | Product |
|---|---|---|---|
| 22 | 3-methoxy cholestene-2 | methyl nitrite | 3,3-dimethoxy-2-oximinocholestane |

We claim:

1. α-Nitrosoketal dimers of the formula

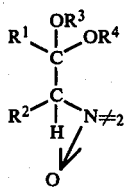

wherein $R^1$ and $R^2$ are selected from the group consisting of $C_1$–$C_{10}$ alkyl or phenyl and/or combinations thereof, or in combination together $R^1$ and $R^2$ are a part of the $C_5$–$C_{12}$ cyclic structures, and $R^3$ and $R^4$ are independently selected from the group consisting of $C_1$–$C_{10}$ alkyl, cyclohexyl and $C_1$–$C_4$ alkyl substituted cyclohexyl radicals.

2. A process for the production of an alphaoximinoketal of the formula

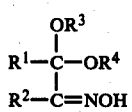

wherein $R^1$ and $R^2$ are selected from the group consisting of $C_1$–$C_{10}$ alkyl, phenyl, combinations thereof, and in combination together $R^1$ and $R^2$ are a part of a $C_5$–$C_{12}$ cyclic structure; and $R^3$ and $R^4$ are independently selected from the group consisting of $C_1$–$C_{10}$ alkyl, cyclohexyl and $C_1$–$C_4$ alkyl substituted cyclohexyl radicals, comprising the steps of:

(a) nitrosating, in the presence of a catalytic amount of a suitable acid and at a temperature of between about $-70°$ C. and $25°$ C. and at a pressure of between about one atmosphere and 200 psi, an alkoxyalkene of the formula

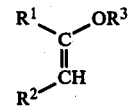

with at least one molar equivalent of an alkyl nitrite of the formula $R^4ONO$ wherein $R^1$, $R^2$, $R^3$ and $R^4$ are as above defined in this claim;

(b) isomerizing the resulting alpha-nitrosoketal dimer to an alpha-oximinoketal above defined in this claim.

3. The process of claim 2 wherein the dimer is isomerized by heating to a temperature above the melting point of the compound.

4. The process of claim 2 wherein the dimer is isomerized by heating in a hydrocarbon solvent at a temperature below the melting point of the compound.

5. The process of claim 4 wherein the dimer is isomerized in the presence of catalytic amount of base.

6. The process of claim 2 wherein the dimer is isomerized by dissolving in an excess of a hydroxylic solvent at about room temperature in the presence of a catalytic amount of base.

7. The process of claim 2 wherein the nitrosation is carried out with 1.10–1.50 molar equivalent of an alkyl nitrite in a solution of an inert solvent and the solvent is removed before isomerization.

8. The process of claim 7 wherein the inert solvent is sulfur dioxide.

* * * * *